(12) United States Patent
Buchanan et al.

(10) Patent No.: US 6,660,896 B1
(45) Date of Patent: Dec. 9, 2003

(54) ISOMERIZATION OF ETHYLBENZENE AND XYLENES

(75) Inventors: John Scott Buchanan, Lambertville, NJ (US); Xiaobing Feng, Houston, TX (US); Gary David Mohr, Houston, TX (US); David L. Stern, Annandale, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/418,439

(22) Filed: Apr. 16, 2003

(51) Int. Cl.[7] .................................................. C07C 5/27
(52) U.S. Cl. ...................... 585/481; 585/480; 585/482; 585/314
(58) Field of Search ................................ 585/480, 481, 585/482, 314

(56) References Cited

U.S. PATENT DOCUMENTS

| 3,354,078 | A |   | 11/1967 | Miale et al. ............... 208/120 |
| 4,899,011 | A |   | 2/1990 | Chu et al. .................. 585/481 |
| 5,028,573 | A |   | 7/1991 | Brown et al. ............... 502/66 |
| 5,276,236 | A |   | 1/1994 | Patton et al. ............... 585/482 |
| 5,689,027 | A |   | 11/1997 | Abichandani et al. ...... 585/481 |
| 5,705,726 | A | * | 1/1998 | Abichandani et al. ...... 585/481 |
| 6,517,807 | B2 |  | 2/2003 | Verduijn et al. ............ 423/709 |

FOREIGN PATENT DOCUMENTS

| EP | 0151351 | 8/1988 | ............ C07C/5/27 |
| EP | 0136133 | 1/1989 | ............ C07C/5/27 |

* cited by examiner

*Primary Examiner*—Thuan Dang

(57) ABSTRACT

In a process for isomerizing a feed comprising ethylbenzene and a mixture of xylene isomers, the feed is first contacted under xylene isomerization conditions with a first catalyst composition to produce an intermediate product having a higher para-xylene concentration than the feed, and then the intermediate product is contacted under ethylbenzene isomerization conditions with a second catalyst composition. The second catalyst composition comprises a hydrogenation-dehydrogenation component and a molecular sieve having 10-membered ring pores and is effective to selectively isomerize at least part of the ethylbenzene in the intermediate product to para-xylene and thereby produce a further product having a para-xylene concentration greater than the equilibrium concentration of para-xylene at said ethylbenzene isomerization conditions.

26 Claims, No Drawings

ISOMERIZATION OF ETHYLBENZENE AND XYLENES

FIELD

This invention relates to a process for the isomerization of xylenes and the selective conversion of ethylbenzene to para-xylene.

BACKGROUND

Para-xylene is a valuable chemical feedstock which may be derived from mixtures of $C_8$ aromatics separated from such raw materials as petroleum naphthas, particularly reformates, usually by selective solvent extraction. The $C_8$ aromatic fractions from these sources vary quite widely in composition but will usually be in the range of 10 to 32 wt. % ethylbenzene (EB) with the balance, xylenes, being divided approximately 50 wt. % meta and 25 wt. % each of para and ortho.

Individual isomer products may be separated from the naturally occurring mixtures by appropriate physical methods. Ethylbenzene may be separated by fractional distillation, although this is a costly operation. Orthoxylene may be separated by fractional distillation, and is so produced commercially. Para-xylene may be separated from the mixed isomers by fractional crystallization, selective adsorption, or membrane separation.

As commercial use of para-xylene has increased, combining physical separation with chemical isomerization of the other xylene isomers to increase the yield of the desired para-isomer has become increasingly important. However, since the boiling point of ethylbenzene is very close to those of para-xylene and meta-xylene, complete removal of ethylbenzene from the $C_8$ aromatic feed by distillation is impractical. Hence an important feature of any commercial xylene isomerization process is the ability to convert ethylbenzene in the feed while simultaneously minimizing any conversion of xylenes to other compounds.

One commercially successful xylene isomerization process is described in U.S. Pat. No. 4,899,011 in which a $C_8$ aromatic feed, which has been depleted in its para-xylene content, is contacted with a two component catalyst system. The first catalyst component selectively dealkylates the ethylbenzene to benzene and ethane, while the second component selectively isomerizes the xylenes to increase the para-xylene content to a value at or approaching the thermal equilibrium value. The first catalyst component comprises a Constraint Index 1–12 molecular sieve, such as ZSM-5, which has an ortho-xylene sorption time of greater than 50 minutes based on its capacity to sorb 30% of the equilibrium capacity of ortho-xylene at 120° C. and an ortho-xylene partial pressure of 4.5±0.8 mm of mercury, whereas the second component comprises a Constraint Index 1–12 molecular sieve which has an ortho-xylene sorption time of less than 10 minutes under the same conditions. Each catalyst component also contains a hydrogenation component, preferably a platinum group metal.

An improvement over the process of U.S. Pat. No. 4,899,011 is described in U.S. Pat. No. 5,689,027 in which the first catalyst component in the two component system is pre-selectivated by coking, or more preferably by deposition of a surface coating of silica, to increase its ortho-xylene sorption time to greater than 1200 minutes under the same conditions as cited in the '011 patent. Using such a system it is found that high ethylbenzene dealkylation rates can be achieved with significantly lower xylene losses than obtained with the process of the '011 patent.

One potential problem of these processes is that the ethylbenzene in the feed is converted via dealkylation to benzene and a $C_2$ fraction. The benzene and $C_2$ fraction must then either be separated from the process stream or converted. Refiners and petrochemical producers are therefore faced with large amounts of benzene by-product which, depending on market conditions, may bring prices below that of the desired xylene product.

Another approach to producing xylenes from a feed stream containing ethylbenzene involves converting the ethylbenzene by isomerization to xylenes. Octafining is one such process where ethylbenzene is converted to xylenes over a catalyst comprising platinum on silica-alumina. In Octafining, ethylbenzene reacts through ethyl cyclohexane to dimethyl cyclohexanes which in turn equilibrate to xylenes. However, competing reactions tend to result in significant losses of $C_8$ aromatics and the amount of para-xylene in the product tends to be at or below equilibrium levels. In addition, catalyst activity tends to decline rapidly especially at high ethylbenzene concentrations in the feed.

U.S. Pat. No. 5,028,573 discloses a dual function composite catalyst for simultaneously isomerizing ethylbenzene and xylenes in a mixed $C_8$ aromatic hydrocarbon feed, wherein the catalyst has an alpha value of 0.005 to 3 and comprises (a) a crystalline aluminosilicate zeolite having a low acid activity as measured by an alpha value of from 0.02 to 11, an average crystal size of not more than 0.4 microns for at least 50% by weight of the crystals, a silica to alumina ratio of at least about 12, a constraint index of about 1 to 12, a xylene sorption capacity greater than 1 gram per 100 grams of zeolite, and an orthoxylene sorption time for 30 percent of said capacity less than 10 minutes, said sorption capacity and sorption time being measured at 120° C. and a xylene pressure of 4.5±0.8 mm of mercury, and (b) a supported metal of Group VIII of the Periodic Table having a hydrogenation/dehydrogenation activity sufficient to provide the catalyst with a dehydrogenation activity of at least 10. The zeolite employed in the catalyst disclosed in U.S. Pat. No. 5,028,573 can include ZSM-5, ZSM-11, ZSM-12, ZSM-22, ZSM-23, ZSM-35 and ZSM-48, with ZSM-5 being particularly preferred.

EP-A-0136133 discloses a process for the isomerization of a feed containing an aromatic $C_8$ mixture of ethylbenzene and xylene by which the paraxylene content is enhanced, said process comprising contacting the feed under conversion conditions with a catalyst comprising ZSM-23 zeolite having pores which are substantially unobstructed by silica.

EP-A-0151351 discloses a process for isomerizing ethylbenzene selectively to provide para-xylene comprising passing ethylbenzene and hydrogen under isomerizing conditions over a catalyst comprising: (a) ZSM-22 or ZSM-23 zeolite; and (b) a hydrogenation/dehydrogenation metal, wherein the hydrogenation/dehydrogenation metal is incorporated in the catalyst after any steaming of the catalyst.

U.S. Pat. No. 5,276,236 discloses that platinum-containing Mg/SAPO-31 can be effective in isomerizing ethylbenzene to xylenes in which the para-isomer is in excess of equilibrium concentration but where, as with most commercial feeds, ortho-xylene is also present, the para content in the product is always less than equilibrium.

Thus, while certain prior art processes have been successful in isomerizing ethylbenzene in a mixed $C_8$ aromatic hydrocarbon feed, there remains a need for a process which has improved selectivity to para-xylene, especially in the presence of a feed containing ortho-xylene, and which can be operated with reduced loss of $C_8$ aromatics.

SUMMARY

The invention resides in a process for isomerizing a feed comprising ethylbenzene and a mixture of xylene isomers, said process comprising (a) contacting said feed under xylene isomerization conditions with a first catalyst composition to produce an intermediate product having a higher para-xylene concentration than the feed, and then (b) contacting at least part of said intermediate product under ethylbenzene isomerization conditions with a second catalyst composition comprising a hydrogenation-dehydrogenation component and a molecular sieve having 10-membered ring pores, said second catalyst composition being effective under said ethylbenzene isomerization conditions to selectively isomerize at least part of the ethylbenzene in said intermediate product to para-xylene and thereby produce a further product having a para-xylene concentration greater than the equilibrium concentration of para-xylene at said ethylbenzene isomerization conditions.

Conveniently, said contacting (a) converts less than 35 wt %, such as less than 20 wt %, of the ethylbenzene in the feed and said contacting (b) converts more than 35 wt %, such as at least 50 wt %, of the ethylbenzene in the intermediate product.

Conveniently, said second catalyst composition has an alpha value of about 0.1 to about 20, such as from about 1 to about 5.

In one embodiment, the second catalyst composition comprises about 0.01 to about 10 wt %, such as about 0.03 to about 3 wt. %, for example about 0.2 to about 1 wt. % of said hydrogenation component. Typically, the hydrogenation component comprises a Group VIII metal, such as platinum.

Conveniently, said molecular sieve is selected from SAPO-11, ZSM-23, ZSM-22, NU-87, ZSM-11, ZSM-50, ZSM-57, SAPO-41, and ZSM-48.

Conveniently, said feed contains about 20 to about 80 wt. %, for example about 25 to about 45 wt. %, of ethylbenzene.

Conveniently, said mixture of xylene isomers comprises less than 90 wt. %, such as less than 60 wt. %, of meta-xylene and conveniently contains about 10 to about 30 wt. % of ortho-xylene.

DETAILED DESCRIPTION OF THE EMBODIMENTS

The present invention provides a two-stage process for isomerizing a feed comprising ethylbenzene and a mixture of xylene isomers, and typically a mixture of xylene isomers depleted in para-xylene. In the first stage of the present process, unlike the two-stage processes of U.S. Pat. Nos. 4,899,011 and 5,689,027, the feed is contacted with a first, xylene isomerization catalyst under xylene isomerization conditions to produce an intermediate product having a higher para-xylene concentration than the feed, preferably with little or no conversion of ethylbenzene in the feed.

In the second stage of the present process, at least part of the intermediate product is contacted with a second, ethylbenzene isomerization catalyst composition under ethylbenzene isomerization conditions so as to selectively isomerize at least part of the ethylbenzene in said intermediate product to para-xylene and thereby produce a further product having a para-xylene concentration greater than the equilibrium concentration of para-xylene at said ethylbenzene isomerization conditions. The second stage of the process is preferably accompanied by little or no isomerization of the xylenes in the intermediate product. The second catalyst composition comprises a hydrogenation-dehydrogenation component and a molecular sieve having 10-membered ring pores.

The present process maximizes the production of para-xylene and minimizes the conversion of $C_8$ aromatics to higher and lower molecular weight products.

Feedstock

In general, the present invention relates to the isomerization of any feed containing ethylbenzene and xylene. In particular, the feed may be any $C_8$ aromatic hydrocarbon feed containing ethylbenzene and a mixture of xylene isomers, such as the $C_8$ fraction derived from catalytic reforming of a petroleum naphtha. Generally, such a feed will have an ethylbenzene content in the range of about 20 to about 80 weight percent, such as about 25 to about 45 weight percent, and the mixture of xylene isomers will contain less than 80 weight percent, such as less than 60 weight percent, of meta-xylene, from about 10 to about 30 orthoxylene and 0 to about 15 weight percent of para-xylene. In addition to the above aromatic $C_8$ mixture, the feed may contain non-aromatic hydrocarbons, e.g., naphthenes and paraffins in an amount up to 30 weight percent.

For example, the feed to the present process may comprise ethylbenzene and a para-depleted mixture of xylenes produced by, for example, subjecting the feed to a para-xylene separation step, such as fractional crystallization.

First Catalyst Composition

The first catalyst composition employed in the present process is not critical but should be arranged to maximize the isomerization of ortho- and meta-xylenes in the feed to para-xylene, while minimizing the conversion of ethylbenzene.

Typically, the first catalyst composition will comprise an intermediate pore size molecular sieve having a Constraint Index within the approximate range of 1 to 12 (e.g., having a less pore size than about 7 Angstroms, such as from about 5 to less than about 7 Angstroms). The method by which Constraint Index is determined is described fully in U.S. Pat. No. 4,016,218, incorporated herein by reference for details of the method.

Examples of intermediate pore size molecular sieves useful in the first catalyst composition include ZSM-5 (U.S. Pat. No. 3,702,886 and Re. 29,948), ZSM-11 (U.S. Pat. No. 3,709,979); ZSM-12 (U.S. Pat. No. 3,832,449; ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780). The entire contents of these patents are incorporated by reference herein.

Alternatively, the first catalyst composition may comprise a molecular sieve selected from MCM-22 (described in U.S. Pat. No. 4,954,325), PSH-3 (described in U.S. Pat. No. 4,439,409), SSZ-25 (described in U.S. Pat. No. 4,826,667), MCM-36 (described in U.S. Pat. No. 5,250,277), MCM-49 (described in U.S. Pat. No. 5,236,575) and MCM-56 (described in U.S. Pat. No. 5,362,697), with MCM-49 being particularly preferred. The entire contents of the above references are incorporated by reference herein.

The first catalyst composition may also include a hydrogenationdehydrogenation component, which may be the same material present in the second, ethylbenzene isomerization catalyst. If the same hydrogenationdehydrogenation component is used in both catalysts, typically this component is present in a lower amount in the first catalyst composition than in the second catalyst composition. More preferably, however, to reduce its ethylbenzene conversion activity, the first catalyst composition does not contain a hydrogenation-dehydrogenation component.

In addition, it may be desirable to combine the molecular sieve of the xylene isomerization catalyst with another material resistant to the temperature and other conditions of the process. Such matrix materials include synthetic or naturally occurring substances as well as inorganic materials such as clay, silica, and/or metal oxides. The metal oxides may be naturally occurring or in the form of gelatinous precipitates or gels including mixtures of silica and metal oxides. Naturally occurring clays which can be composited with the molecular sieve include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the molecular sieve may be composited with a porous matrix material, such as alumina, silica-alumina, silica-magnesia, silica-zirconia, silica-thoria, silica-berylia, silica-titania, as well as ternary compounds such as silica-alumina-thoria, silica-alumina-zirconia, silicaalumina-magnesia, and silica-magnesia-zirconia. A mixture of these components could also be used. The matrix may be in the form of a cogel. The relative proportions of molecular sieve component and inorganic oxide gel matrix on an anhydrous basis may vary widely with the molecular sieve content ranging from between about 1 to about 99 percent by weight and more usually in the range of about 10 to about 80 percent by weight of the dry composite.

The first catalyst composition typically has an alpha value of about 4 to about 1000, such as from about 5 to about 80, with the preferred value being inversely dependent on reactor temperature. The "alpha value" of a catalyst reflects the relative activity of the catalyst with respect to a high activity silicaalumina cracking catalyst. The alpha value test is described in U.S. Pat. No. 3,354,078; in the *Journal of Catalysis*, Vol. 4, p. 527 (1965); Vol. 6, p. 278 (13966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395. The higher alpha values correspond with a more active cracking catalyst.

Alpha values for aluminosilicate and silicoaluminophosphate molecular sieves can be controlled to within the above ranges by suitable selection of the $SiO_2/Al_2O_3$ ratio of the sieve, with higher ratios producing lower alpha values as well known in the art. It is also possible to adjust and in particular reduce the alpha value of a molecular sieve by subjecting the sieve to one or more acidity reducing treatments, such as by steaming, partial exchange with such cations as alkali metals, and like known sodium exchange techniques. Examples of such techniques are described in, for example, U.S. Pat. Nos. 3,899,544, 3,960,978, 3,965,209, 4,105,537 and 4,224,141, the entire contents of which are incorporated herein by reference.

Second Catalyst Composition

The second catalyst composition is primarily intended to isomerize the ethylbenzene in the feed selectively to para-xylene, while minimizing isomerization of the xylenes in the feed. The second catalyst composition typically comprises a molecular sieve having unidimensional 10-membered ring pores. The phrase "unidimensional 10-membered ring pores" means that the pores of the molecular sieve are defined by 10-membered rings of tetrahedrally coordinated atoms which extend essentially in one dimension so that the pores are substantially free from any intersecting pores.

Examples of suitable molecular sieves having unidimensional 10-membered ring pores include SAPO-11, ZSM-23, ZSM-22, NU-87, ZSM-11, ZSM-50, ZSM-57, SAPO-41, and ZSM-48. SAPO-11 and a method of its synthesis are described in U.S Pat. No. 4,440,871. ZSM-23 and a method of its synthesis are described in U.S Pat. No. 4,076,842. ZSM-48 and a method of its synthesis are described in U.S Pat. No. 4,397,827. Each of these patents is incorporated herein by reference.

The molecular sieve of the second catalyst composition typically has an alpha value of about 0.1 to about 20, for example from about 1 to about 5.

The molecular sieve used in the second catalyst composition is associated with a hydrogenation-dehydrogenation component. Examples of such components include the oxide, hydroxide, sulfide, or free metal (i.e., zerovalent) forms of Group VIII metals (i.e., Pt, Pd, Ir, Rh, Os, Ru, Ni, Co and Fe), Group VIB metals (i.e, Cr, Mo, W), Group IVA metals (i.e., Sn and Pb), Group VA metals (i.e., Sb and Bi), and Group VIIB metals (i.e., Mn, Tc and Re). Combinations of catalytic forms of such noble or non-noble metals, such as combinations of Pt with Sn, may be used. The metal is preferably in a reduced valence state. The reduced valence state of the metal may be attained, in situ, during the course of the reaction, when a reducing agent, such as hydrogen, is included in the feed to the reaction. Treatments such as coking or sulfiding may also be employed, especially at the start of a run with fresh catalyst, to modify the catalytic performance of the metal.

In one practical embodiment, the hydrogenation-dehydrogenation component is a noble metal (i.e., Pt, Pd, Ir, Rh, Os and Ru) and particularly is platinum.

The hydrogenation/dehydrogenation component may be incorporated into the catalyst by methods known in the art, such as ion exchange, impregnation or physical admixture. For example, solutions of appropriate metal salts may be contacted with the remaining catalyst components, either before or after selectivation of the catalyst, under conditions sufficient to combine the respective components. The metal containing salt is conveniently water-soluble. Examples of such salts include chloroplatinic acid, tetraamineplatinum complexes, platinum chloride, tin sulfate and tin chloride. The metal may be incorporated in the form of a cationic, anionic or neutral complex such as $Pt(NH_3)_4^{2+}$ and cationic complexes of this type will be found convenient for exchanging metals onto the molecular sieve. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraamine platinum(II) chloride. Anionic complexes such as the metatungstate, permanganate or perrhenate ions are also useful for impregnating metals onto the molecular sieves. After incorporation of the metal, the catalyst can then be filtered, washed with water and calcined at temperatures of from about 250 to about 500° C.

The amount of the hydrogenation-dehydrogenation component is suitably from about 0.001 to about 10 percent by weight, e.g, from about 0.03 to about 3 percent by weight, such as from about 0.2 to about 1 percent by weight of the total catalyst although this will, of course, vary with the nature of the component, with less of the highly active noble metals, particularly platinum, being required than of the less active base metals.

The second catalyst composition may also include a binder and/or matrix material which may be the same as, or different from, any binder and/or matrix material contained by the first catalyst composition. In particular, the binder in the second catalyst composition may be a zeolitic material such that the second catalyst composition comprises a so-called "zeolite-bound zeolite" as described in, for example, U.S. Pat. No. 6,517,807, the entire contents of which are incorporated herein by reference. Thus, the second catalyst composition may comprise a core zeolite having unidimensional 10-membered ring pores, such as ZSM-48, bound with a high silica binder which is at least partly converted to a high silica zeolite (such as ZSM-5 or ZSM-48) which at least partly covers the surface of the core zeolite. By ensuring that the zeolitic binder has a higher silica to alumina molar ratio than the core zeolite, the binder can lower the surface activity of the core zeolite and hence reduce any unwanted xylene isomerization which would otherwise occur at the surface of the core zeolite.

In general, the second catalyst composition is different from the first catalyst composition, for example by containing a different molecular sieve, having a lower alpha value and/or by containing more or a more active hydrogenation/dehydrogenation component. Process Conditions The conditions employed in the xylene isomerization stage of the present process are not narrowly defined but generally include a temperature of from 250 to about 600° C., a pressure of from about 0 to about 500 psig (100 to 3550 kPa), a weight hourly space velocity (WHSV) of between about 0.05 and about 50 $hr^{-1}$, and a hydrogen, $H_2$, to hydrocarbon, HC, molar ratio of between about 0.05 and about 20. Typically, the xylene isomerization step is conducted in the liquid phase under conditions including a temperature of from about 250 to about 400° C., a pressure of from about 50 to about 400 psig psig (445 to 2870 kPa), a WHSV of between about 1 and about 10 $hr^{-1}$, and a $H_2$ to HC molar ratio of between about 1 and about 10. In general, the conditions employed in the xylene isomerization stage are such as to convert less than 35 wt. %, and more typically less than 20 wt. %, of the ethylbenzene in the feed and to produce a para approach to equilibrium (PATE) greater than 80% (preferably greater than 95%). PATE defined as:

$(PX_{PRODUCT}-PX_{FEED}/PX_{EQUILIBRIUM}-PX_{FEED})\times 100$ where $PX_{PRODUCT}$ is the percent para-xylene in the isomerization product by weight of the total xylenes in the product;

where $PX_{FEED}$ is the percent para-xylene in the isomerization feed by weight of the total xylenes in the feed; and $PX_{EQUILIBRIUM}$ is the percent para-xylene by weight of the total xylenes in an equilibrium mixture of xylenes at the reactor temperature.

The conditions used in the ethylbenzene isomerization stage are also not narrowly defined, but generally include a temperature of from about 250 to about 600° C., a pressure of from about 0 to about 500 psig (100 to 3550 kPa), a weight hourly space velocity (WHSV) of between about 0.01 and about 20 $hr^{-1}$, and a hydrogen, $H_2$, to hydrocarbon, HC, molar ratio of between about 0.05 and about 20. Typically, the conditions include a temperature of from about 400 to about 500° C., a pressure of from about 50 to about 400 psig (445 to 2870 kPa), a WHSV of between about 1 and about 10 hr–1, and a $H_2$ to HC molar ratio of between about 1 and about 10. In general, the conditions are selected so that the ethylbenzene conversion per pass is greater than 35% and typically greater than 45%.

In general, the xylene isomerization step and the ethylbenzene isomerization step of the present process are carried out in fixed bed reaction zones containing the catalyst compositions described above. The reaction zones may be in sequential beds in a single reactor, with the ethylbenzene isomerization catalyst being located downstream of the xylene isomerization catalyst and with the feed being cascaded from the first to the second bed without intervening separation of light gases. As an alternative, the ethylbenzene isomerization catalyst and the xylene isomerization catalyst can be disposed in separate reactors which, if desired, can be operated at different process conditions, in particular with the temperature of the ethylbenzene isomerization reactor being higher than that of the xylene isomerization reactor.

In a further embodiment, the process can comprise three or more stages, with a first xylene isomerization stage using the first catalyst composition described above, a final ethylbenzene isomerization stage using the second catalyst composition described above and at least one intermediate stage using a mixture of the first and second catalyst compositions.

The isomerization product can be treated to isolate para-xylene and/or other desirable xylene(s). Thus, for example, the isomerized product can be fed to a variety of para-xylene recovery units, such as a crystallizer, a membrane separation unit, or a selective adsorption unit, and thus the para-xylene may be isolated and recovered. The residual isomerizate can be stripped of products lighter than $C_8$. Products heavier than $C_8$ in the residual isomerizate can be further processed or may be fractionated out. $C_8$ fractions from which para-xylene has been removed can be recycled to the process. Napthenes are typically recycled to extinction in the process of the invention.

Using the process of this invention, it is found that the ethylbenzene in a feed containing a mixture of xylenes in which the meta-xylene content is less than 90% can be selectively converted to para-xylene such that the para approach to equilibrium (PATE) is in excess of 105%. In addition, the amount of conversion of ethylbenzene to benzene and light products is minimized and typically is less than 20 weight percent, such as less than 10 weight percent.

The invention will now be more particularly described with reference to the accompanying Examples.

EXAMPLE 1

A first catalyst composition is prepared by binding ZSM-5 crystals with alumina and forming the resultant mixture into cylindrical extrudates containing 60 wt % ZSM-5 and 40 wt % alumina and having a diameter of about 1/16". The bound ZSM-5 extrudates are then steamed at 1100° F. (593° C.) for sufficient time to produce a catalyst with an alpha of about 10. No metal is added to this catalyst.

EXAMPLE 2

A second catalyst composition is prepared by binding ZSM-48 crystals with alumina and forming the resultant mixture into cylindrical extrudates containing 60 wt % ZSM-48 and 40 wt % alumina and having a diameter of about 1/16". The bound ZSM-48 extrudates are then steamed at 1200° F. (650° C.) for 12 hours to give a base catalyst with an alpha of about 2. About 0.5 wt % Pt is then added to the base catalyst via impregnation with an aqueous solution of tetraamine platinum nitrate.

EXAMPLE 3

A reactor is loaded with 1 g of the first catalyst composition, followed by 2 g of the second catalyst composition. The layered catalyst mixture is used to isomerize a feed consisting of 60% ethylbenzene, 27% m-xylene, and 13% o-xylene, with the feed contacting the first catalyst composition before the second catalyst composition. The isomerization conditions include a temperature of 400° C., a pressure of 200 psig (1480 kPa) and a molar H2/hydrocarbon ratio of 4. The space velocity is adjusted to obtain an overall conversion of about 60% of the ethylbenzene in the feed mixture, primarily to a mixture of xylenes and naphthenes. The amount of p-xylene in the xylene component of the product is about 29%, which is significantly higher than the equilibrium concentration of para-xylene at the reaction conditions (about 24%).

What is claimed is:

1. A process for isomerizing a feed comprising ethylbenzene and a mixture of xylene isomers, said process comprising
    (a) contacting said feed under xylene isomerization conditions with a first catalyst composition to produce an intermediate product having a higher para-xylene concentration than the feed, and then
    (b) contacting at least part of said intermediate product under ethylbenzene isomerization conditions with a second catalyst composition comprising a hydrogenation-dehydrogenation component and a molecular-sieve having 10-membered ring pores, said second catalyst composition being effective under said ethylbenzene isomerization conditions to selectively isomerize at least part of the ethylbenzene in said intermediate product to para-xylene and thereby produce a further product having a para-xylene concentration greater than the equilibrium concentration of para-xylene at said ethylbenzene isomerization conditions.

2. The process of claim 1, wherein feed contains about 20 to about 80 wt % ethylbenzene.

3. The process of claim 1, wherein said feed contains about 25 to about 45 wt % of ethylbenzene.

4. The process of claim 1, wherein said mixture of xylene isomers comprises less than 90 wt % of meta-xylene.

5. The process of claim 1, wherein said mixture of xylene isomers comprises less than 60 wt % of meta-xylene.

6. The process of claim 1, wherein said mixture of xylene isomers comprises about 10 to about 30 wt % of ortho-xylene.

7. The process of claim 1, wherein said contacting (a) converts less than 35 wt % of the ethylbenzene in the feed and said contacting (b) converts more than 35 wt % of the ethylbenzene in the intermediate product.

8. The process of claim 1, wherein said contacting (a) converts less than 20 wt % of the ethylbenzene in the feed and said contacting (b) converts at least 50 wt % of the ethylbenzene in the intermediate product.

9. The process of claim 1, wherein said first catalyst composition comprises a molecular sieve having a Constraint Index within the approximate range of 1 to 12.

10. The process of claim 1, wherein said first catalyst composition has an alpha value of about 5 to about 80.

11. The process of claim 1, wherein the molecular sieve of said second catalyst composition has unidimensional 10-membered ring pores.

12. The process of claim 1, wherein the molecular sieve of said second catalyst composition is selected from SAPO-11, ZSM-23, ZSM-22, NU-87, ZSM11, ZSM-50, ZSM-57, SAPO-41, ZSM-48 and mixtures thereof.

13. The process of claim 1, wherein the molecular sieve of said second catalyst composition includes ZSM-48.

14. The process of claim 1, wherein said second catalyst composition comprises ZSM-48 core bound with ZSM-5 having a higher silica to alumina molar ratio than the ZSM-48.

15. The process of claim 1, wherein said second catalyst composition comprises about 0.01 to about 10 wt % of said hydrogenation component.

16. The process of claim 1, wherein said second catalyst composition comprises about 0.03 to about 3 wt % of said hydrogenation component.

17. The process of claim 1, wherein said second catalyst composition comprises about 0.2 to about 1 wt % of said hydrogenation component.

18. The process of claim 1, wherein said hydrogenation component comprises a Group VIII metal.

19. The process of claim 1, wherein said hydrogenation component comprises platinum.

20. The process of claim 1, wherein the molecular sieve of the second catalyst composition has an alpha value of about 0.1 to about 20.

21. The process of claim 1, wherein the molecular sieve of the second catalyst composition has an alpha value of about 1 to about 5.

22. The process of claim 1, wherein the second catalyst composition is different from said first catalyst composition.

23. The process of claim 1, wherein said xylene isomerization conditions include a temperature of from about 250 to about 600° C., a pressure of from about 0 to about 500 psig (100 to 3550 kPa), a weight hourly space velocity (WHSV) of between about 0.05 and about 50 hr$^{-1}$, and a hydrogen, $H_2$, to hydrocarbon, HC, molar ratio of between about 0.05 and about 20.

24. The process of claim 1, wherein said ethylbenzene isomerization conditions include a temperature of from about 250 to about 600° C., a pressure of from about 0 to about 500 psig (100 to 3550 kPa), a weight hourly space velocity (WHSV) of between about 0.01 and about 20 hr$^{-1}$, and a hydrogen, $H_2$, to hydrocarbon, HC, molar ratio of between about 0.05 and about 20.

25. A process for isomerizing a feed comprising ethylbenzene and a mixture of xylene isomers, said process comprising
    (a) contacting said feed under xylene isomerization conditions with a first catalyst comprising ZSM-5 to produce an intermediate product having a higher para-xylene concentration than the feed, and then
    (b) contacting at least part of said intermediate product under ethylbenzene isomerization conditions with a second catalyst composition comprising a hydrogenation-dehydrogenation component and a molecular sieve selected from the group consisting of SAPO-11, ZSM-23, ZSM-22, NU-87, ZSM11, ZSM-50, ZSM-57, SAPO-41, ZSM-48 and mixtures thereof to produce a further product having a para-xylene concentration greater than the equilibrium concentration of para-xylene at said ethylbenzene isomerization conditions.

26. The process of claim 25, wherein the molecular sieve of said second catalyst composition is ZSM-48.

* * * * *